US008940727B2

United States Patent
Kan et al.

(10) Patent No.: US 8,940,727 B2
(45) Date of Patent: Jan. 27, 2015

(54) BENZAZEPINE COMPOUND

(75) Inventors: Keizo Kan, Osaka (JP); Tadaaki Ohtani, Osaka (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 13/504,101

(22) PCT Filed: Oct. 25, 2010

(86) PCT No.: PCT/JP2010/068807
§ 371 (c)(1),
(2), (4) Date: Jun. 13, 2012

(87) PCT Pub. No.: WO2011/052519
PCT Pub. Date: May 5, 2011

(65) Prior Publication Data
US 2013/0131045 A1    May 23, 2013

(30) Foreign Application Priority Data

Oct. 26, 2009  (JP) ................. 2009-245434

(51) Int. Cl.
*C07D 223/16*  (2006.01)
*A61K 31/55*  (2006.01)
*A61K 45/06*  (2006.01)

(52) U.S. Cl.
CPC .............. *C07D 223/16* (2013.01); *A61K 31/55* (2013.01); *A61K 45/06* (2013.01)
USPC .................................................. 514/213.01

(58) Field of Classification Search
USPC .................................................. 514/213.01
See application file for complete search history.

(56) References Cited

U.S. PATENT DOCUMENTS

| 5,258,510 | A | 11/1993 | Ogawa et al. |
| 5,753,677 | A | 5/1998 | Ogawa et al. |
| 5,856,564 | A | 1/1999 | Tanaka et al. |

FOREIGN PATENT DOCUMENTS

| JP | 04-321669 | A | 11/1992 |
| JP | 7-076214 | B2 | 8/1995 |
| JP | 2905909 | B2 | 4/1999 |
| JP | 2009-502963 | A | 1/2009 |
| SU | 2129123 | C1 | 4/1990 |
| WO | 2007/016431 | A2 | 2/2007 |
| WO | 2007/143468 | A2 | 12/2007 |
| WO | 2008/049116 | A2 | 4/2008 |
| WO | 2009/001968 | A1 | 12/2008 |
| WO | 2009/117144 | A1 | 9/2009 |

OTHER PUBLICATIONS

Gheorghiade (Effects of Tolvaptan, a Vasopressin Antagonist, in Patients Hospitalized with Worsening Heart Failure, JAMA, Apr. 2004, vol. 291, No. 16).*
Heterocycles, vol. 54, No. 1, pp. 131-138.
Journal of High Technology Law, vol. X, No. 1, pp. 22-74.
Kazumi Kondo, et al., "7-Chloro-5-hydroxy-1-[2-methyl-4-(2-methylbenzoyl-amino)benzoyl]-2,3,4,5-tetrahydro-1 H-1-benzazepine (OPC-41061): A Potent, Orally Active Nonpeptide Arginine Vasopressin $V_2$ Receptor Antagonist", Bioorganic & Medicinal Chemistry, 1999, pp. 1743-1754, vol. 7, No. 8.
Yoshitaka Yamamura, et al., "OPC-41061, a Highly Potent Human Vasopressin $V_2$-Receptor Antagonist: Pharmacological Profile and Aquaretic Effect by Single and Multiple Oral Dosing in Rats", The Journal of Pharmacology and Experimental Therapeutics, 1998, pp. 860-867, vol. 287, No. 3.
Shoaf, S.E. et al., "Tolvaptan Administration Does Not Affect Steady State Amiodarone Concentrations in Patients With Cardiac Arrhythmias", J Cardiovascular Pharmacology and Therapeutics, vol. 10, No. 3, pp. 165-171, 2005.
U.S. FDA, Application No. NDA 22275, Clinical pharmacology and biopharmaceutics review, pp. 1-60, Aug. 22, 2008.
Concert Pharmaceuticals et al., Precision Deuterium Chemistry Backgrounder, 2007, pp. 1-6.
Supplementary European Search Report dated Feb. 25, 213 in European Patent Application No. 10826651.1.
Heterocycles, vol. 54, No. 1, pp. 131-138, 2001.
Journal of High Technology Law, vol. X, No. 1, pp. 22-74, 2009.

* cited by examiner

*Primary Examiner* — San-Ming Hui
*Assistant Examiner* — Kathrien Cruz
(74) *Attorney, Agent, or Firm* — Sughrue Mion, PLLC

(57) ABSTRACT

An object of the present invention is to provide a novel benzazepine compound or a salt thereof, which has excellent vasopressin antagonistic activity.
The benzazepine compound or a salt thereof of the present invention is represented by Formula (1):

wherein $R^1$, $R^2$ and $R^5$ may be the same or different and each represents H or D; and $R^3$ and $R^4$ each represents a $C_{1-6}$ alkyl group, a $C_{1-6}$ deuteroalkyl group, or a $C_{1-6}$ perdeuteroalkyl group.

8 Claims, No Drawings

BENZAZEPINE COMPOUND

CROSS REFERENCE TO RELATED APPLICATIONS

This application is a National Stage of International Application No. PCT/JP2010/068807 filed Oct. 25, 2010, claiming priority based on Japanese Patent Application No. 2009-245434 filed Oct. 26, 2009, the contents of all of which are incorporated herein by reference in their entirety.

TECHNICAL FIELD

The present invention relates to a benzazepine compound.

BACKGROUND ART

Heretofore, several compounds having a vasopressin antagonistic activity have been developed (e.g., Patent Literature 1 to 3 and Non-Patent Literature 1 and 2). However, the development of a compound having more excellent vasopressin antagonistic activity is in demand.

Patent Literature 3 discloses, in Example 430, compounds exhibiting excellent vasopressin antagonistic activity. Of such compounds, tolvaptan, represented by the following formula, is also disclosed.

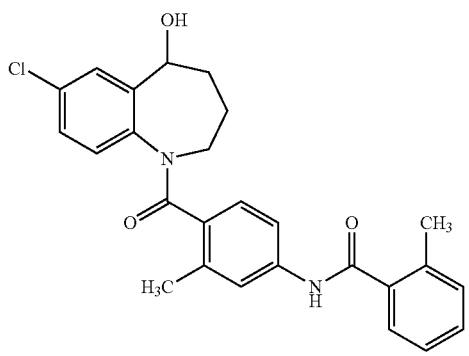

However, Patent Literature 3 is silent about the deuterated compound of the present invention.

CITATION LIST

Patent Literature

PTL 1: WO 2009/117144
PTL 2: Japanese Examined Patent Publication No. H7-76214
PTL 3: Japanese Patent No. 2905909

Non-Patent Literature

NPL 1: Kondo, K.; Ogawa, H.; Yamashita, H.; Miyamoto, H.; Tanaka, M.; Nakaya, K.; Kitano, K.; Yamamura, Y.; Nakamura, S.; Onogawa, T.; Mori, T.; Tominaga, M.; Bioorganic & Medicinal Chemistry, 1999, 7(8), 1743-1757
NPL 2: Yamamura, Y.; Nakamura, S.; Itoh, S.; Hirano, T.; Onogawa, T.; Yamashita, T.; Yamada, Y.; Tsujimae, K.; Aoyama, M.; Kotosai, K.; Ogawa, H.; Yamashita, H.; Kondo, K.; Tominaga, M.; Tsujimoto, G.; Mori, T.; Journal of Pharmacology and Experimental Therapeutics, 1998, 287(3), 860-867

SUMMARY OF INVENTION

Technical Problem

An object of the present invention is to provide a novel benzazepine compound having more excellent vasopressin antagonistic activity than tolvaptan, and having additional benefits, e.g., achieving a further extended pharmacological effective life by producing the compound with high metabolic stability.

Solution to Problem

The present inventors have conducted extensive research to achieve the above objects. Consequently, the present inventor found that by converting tolvaptan into its D-form, a novel benzazepine compound represented by Formula (1) below has more excellent vasopressin antagonistic activity and metabolic stability. The present invention was accomplished based on such findings.

Item 1.

A benzazepine compound represented by Formula (1):

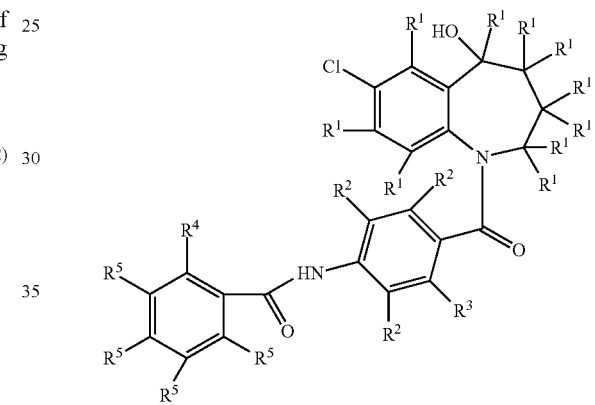

or a salt thereof,
wherein $R^1$ may be the same or different and each represents H or D,
$R^2$ may be the same or different and each represents H or D,
$R^3$ represents a $C_{1-6}$ alkyl group, a $C_{1-6}$ deuteroalkyl group or a $C_{1-6}$ perdeuteroalkyl group,
$R^4$ represents a $C_{1-6}$ alkyl group, a $C_{1-6}$ deuteroalkyl group or a $C_{1-6}$ perdeuteroalkyl group,
$R^5$ may be the same or different and each represents H or D.

Item 2. A benzazepine compound selected from the group consisting of:
(1) N-(4-(7-chloro-5-hydroxy-2,3,4-trihydro-5-deutero-1H-benzo[b]azepine-1-carbonyl)-3-methylphenyl)-2-methylbenzamide,
(2) N-(4-(7-chloro-2,3-dihydro-5-hydroxy-4,4,5-trideutero-1H-benzo[b]azepine-1-carbonyl)-3-methylphenyl)-2-methylbenzamide,
(3) N-(4-(7-chloro-5-hydroxy-2,2-dideutero-3,4,5-trihydro-1H-benzo[b]azepine-1-carbonyl)-3-methylphenyl)-2-methylbenzamide,
(4) N-(4-(7-chloro-5-hydroxy-2,2,4,4,5-pentadeutero-1H-benzo[b]azepine-1-carbonyl)-3-methylphenyl)-2-methylbenzamide, and
(5) N-{4-(7-chloro-5-hydroxy-2,3,4,5-tetrahydro-1H-benzo[b]azepine-1-carbonyl)-3-methylphenyl}-3,4,5,6-tetradeutero-2-trideutero methylbenzamide,
or a salt thereof.

Item 3. A pharmaceutical composition or a salt thereof comprising, as an active ingredient, the benzazepine compound of Item 1 or 2, and a pharmaceutically acceptable carrier.

Item 4. Use of the benzazepine compound or a salt thereof of Item 1 or 2, as a drug.

Item 5. A vasopressin antagonist comprising, as an active ingredient, the benzazepine compound or a salt thereof of Item 1 or 2.

Item 6. The pharmaceutical composition according to Item 3, which is for preventing or treating at least one disease selected from the group consisting of hypertension, edema, ascites, heart failure, renal dysfunction, syndrome of inappropriate secretion of antidiuretic hormone (SIADH), liver cirrhosis, hyponatremia, hypokalemia, diabetes, circulatory failure, motion sickness, water-metabolism disorder, renal failure, cerebral infarction, cardiac infarction, and polycystic kidney disease (PKD).

Item 7. The pharmaceutical composition according to Item 3, which is for use as at least one drug selected from the group consisting of vasodilators, antihypertensive agents, water-diuretic agents, platelet aggregation inhibitors, ureotelic agents, anti-heart failure agents, and anti-renal failure agents.

Item 8. A method for preventing or treating at least one disease selected from the group consisting of hypertension, edema, ascites, heart failure, renal dysfunction, syndrome of inappropriate secretion of vasopressin (syndrome of inappropriate secretion of antidiuretic hormone: SIADH), liver cirrhosis, hyponatremia, hypokalemia, diabetes, circulatory failure, motion sickness, water-metabolism disorder, renal failure, cerebral infarction, cardiac infarction, and polycystic kidney diseases (PKD), the method comprising administering the benzazepine compound or a salt thereof of Item 1 or 2, to a human or animal.

The present invention provides a benzazepine compound represented by Formula (1) above or a salt thereof.

Specific examples of the $C_{1-6}$, preferably $C_{1-3}$, alkyl groups represented by $R^3$ and $R^4$ in Formula (1) include methyl group, ethyl group, n-propyl group, iso-propyl group, and the like.

The $C_{1-6}$, preferably $C_{1-3}$, deuteroalkyl groups represented by $R^3$ and $R^4$ in Formula (1) are those in which at least one hydrogen atom of the alkyl group is substituted with a deuterium atom (with the proviso that those in which all of the hydrogen atoms of the alkyl group are substituted with deuterium atoms are excluded).

Specific examples thereof include those represented by the formula:

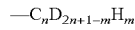

$$-C_nD_{2n+1-m}H_m$$

wherein n is an integer of 1 to 6, preferably 1 to 3, and m is an integer of 1 to 2n. More specifically, examples thereof include deuteromethyl group, dideuteromethyl group, deuteroethyl group, dideuteroethyl group, trideuteroethyl group, tetradeuteroethyl group, deuteropropyl group, dideuteropropyl group, trideuteropropyl group, tetradeuteropropyl group, pentadeuteropropyl group, and the like.

Specific examples of the $C_{1-6}$, preferably $C_{1-3}$, perdeuteroalkyl groups represented by $R^3$ and $R^4$ in Formula (1) include perdeuteromethyl group, perdeuteroethyl group, perdeutero-n-propyl group, perdeutero-iso-propyl group, and the like.

The benzazepine compound of the present invention or a salt thereof is produced by a method disclosed in the Reference Examples and Examples, or in accordance with these methods.

The benzazepine compound of the present invention obtained by these methods can be separated from the reaction system by a general separation means, and can further be purified. As such a separation and purification means, for example, a distillation method, a recrystallization method, column chromatography, ion-exchange chromatography, gel chromatography, affinity chromatography, preparative thin-layer chromatography, a solvent extraction method, or the like, can be employed.

The benzazepine compound of the present invention can form suitable salts. Examples of such suitable salts include suitable salts of a compound (1) exemplified below.

The suitable salts of the compound (1) are pharmacologically acceptable salts. Examples thereof include alkali metal salts (e.g., sodium salt and potassium salt), alkaline earth metal salts (e.g., calcium salt and magnesium salt) and like metal salts; ammonium salts, alkali metal carbonates (e.g., lithium carbonate, potassium carbonate, sodium carbonate, and cesium carbonate), alkali metal hydrogen carbonates (e.g., lithium hydrogen carbonate, sodium hydrogen carbonate, and potassium hydrogen carbonate), alkali metal hydroxides (e.g., lithium hydroxide, sodium hydroxide, potassium hydroxide, and cesium hydroxide), and like salts of inorganic bases; for example, tri(lower)alkylamines (e.g., trimethylamine, triethylamine, and N-ethyldiisopropylamine), pyridine, quinoline, piperidine, imidazol, picoline, dimethylaminopyridine, dimethylaniline, N-(lower)alkyl-morpholine (e.g., N-methylmorpholine), 1,5-diazabicyclo[4.3.0]nonene-5 (DBN), 1,8-diazabicyclo[5.4.0]undecene-7 (DBU), 1,4-diazabicyclo[2.2.2]octane (DABCO), trishydroxymethylaminomethane, and like salts of organic bases; and hydrochloride, hydrobromate, hydroiodide, sulfate, nitrate, phosphate, and like salts of inorganic acids; formate, acetate, propionate, oxalate, malonate, succinate, fumarate, maleate, lactate, malate, citrate, tartrate, carbonate, picrate, methanesulfonate, ethanesulfonate, p-toluenesulfonate, glutamate, and like salts of organic acids; and the like.

The benzazepine compound of the present invention also includes those in the form of a solvate with a solvent (e.g., hydrate or ethanol solvate). Examples of preferable solvates include hydrate.

The compounds of the present invention represented by Formula (1) also naturally include isomers, such as geometrical isomers, stereoisomers, and optical isomers.

The compound of Formula (1) and a salt thereof are used in the form of common pharmaceutical preparations. Such pharmaceutical preparations can be prepared by using usually employed diluents and excipients, such as fillers, extenders, binders, wetting agents, disintegrants, surfactants, and lubricants. The form of such pharmaceutical preparations can be selected from various forms, depending on the therapeutic purpose. Typical examples thereof include tablets, pills, powders, solutions, suspensions, emulsions, granules, capsules, suppositories, injections (solutions, suspensions, etc.), and the like.

To form tablets, a wide range of carriers known in this field can be used, including, for example, lactose, sucrose, sodium chloride, glucose, urea, starch, calcium carbonate, kaolin, crystalline cellulose, silicic acid, and like excipients; water, ethanol, propanol, simple syrup, glucose solutions, starch solutions, gelatin solutions, carboxymethylcellulose, shellac, methylcellulose, potassium phosphate, polyvinylpyrrolidone, and like binders; dry starch, sodium alginate, agar powder, laminaran powder, sodium hydrogen carbonate, calcium carbonate, polyoxyethylene sorbitan fatty acid esters, sodium lauryl sulfate, stearic acid monoglyceride, starch, lactose, and like disintegrants; sucrose, stearin, cacao butter, hydrogenated oils, and like disintegration inhibitors; quaternary ammonium base, sodium lauryl sulfate, and like absorption promoters; glycerin, starch, and like wetting agents; starch, lactose, kaolin, bentonite, colloidal silica, and like adsorbents; purified talc, stearates, boric acid powder, polyethylene glycol, and like lubricants; and the like. Such tablets may be coated with usual coating materials as required, to prepare, for example, sugar-coated tablets, gelatin-coated tablets, enteric-coated tablets, film-coated tablets, or double- or multi-layered tablets.

To form pills, a wide range of carriers known in this field can be used. Examples thereof include glucose, lactose, starch, cacao butter, hydrogenated vegetable oils, kaolin, talc, and other excipients; gum arabic powder, tragacanth powder, gelatin, ethanol, and other binders; laminaran, agar, and other disintegrants; etc.

To form suppositories, a wide range of known carriers can be used. Examples thereof include polyethylene glycol, cacao butter, higher alcohols, esters of higher alcohols, gelatin, semi-synthetic glycerides, etc.

Capsules can be prepared according to a known method, by mixing a usual active ingredient compound with an aforementioned carrier, and encapsulating the resulting mixture into a hard gelatin capsule, soft gelatin capsule, or the like.

To form an injection, a solution, emulsion, or suspension is sterilized and preferably made isotonic to blood. Any diluent commonly used in this field can be employed to form the injection. Examples of such diluents include water, ethanol, macrogol, propylene glycol, ethoxylated isostearyl alcohol, polyoxylated isostearyl alcohol, fatty acid esters of polyoxyethylene sorbitan, etc.

In this case, the pharmaceutical preparation may contain sodium chloride, glucose, or glycerol in an amount sufficient to prepare an isotonic solution, and may contain typical solubilizers, buffers, analgesic agents, etc., and may further contain, if necessary, coloring agents, preservatives, flavors, sweetening agents, etc., and/or other medicines.

The amount of the compound of Formula (1) or a salt thereof contained in the pharmaceutical preparation of the present invention is not limited and can be suitably selected from a wide range. The pharmaceutical preparation usually contains the compound or a salt thereof in a proportion of usually about 0.1 to 70 wt %, and preferably about 0.1 to 30 wt %.

The route of administration of the pharmaceutical preparation of the present invention is not particularly limited, and the preparation is administered by, for example, a route suitable for the form of the preparation, the patient's age, sex, and other conditions, and the severity of the disease. For example, tablets, pills, solutions, suspensions, emulsions, granules, and capsules are administered orally. Injections are intravenously administered singly or in combination with typical injection transfusions such as glucose solutions, amino acid solutions or the like. Further, injections are singly administered intramuscularly, intracutaneously, subcutaneously, or intraperitoneally, if necessary. Suppositories are administered intrarectally.

The dosage of the pharmaceutical preparation of the invention is suitably selected according to the method of use, the patient's age, sex, and other conditions, and the severity of the disease. The amount of active ingredient compound is usually about 0.1 to 10 mg/kg body weight/day. Further, it is desirable that the pharmaceutical preparation in each unit of the administration form contains the active ingredient compound in an amount of about 1 to 200 mg.

Advantageous Effects of Invention

The benzazepine compound of the present invention exhibits excellent vasopressin antagonistic activity. The specific effects of the vasopressin antagonistic activity include, for example, a vasodilating effect, a hypotensive effect, an inhibitory effect on hepatic glucose release, an inhibitory effect on mesangial cell growth, a water diuretic effect, a platelet aggregation inhibitory effect, an inhibitory effect on vomiting, a ureotelic effect, an inhibitory effect on secretion of factor VIII, a cardiac function increasing effect, an inhibitory effect on mesangial cell contraction, an inhibitory effect on hepatic glucose production, an inhibitory effect on aldosterone secretion, an inhibitory effect on endothelin production, a regulatory effect on renin secretion, a memory modulation effect, a thermoregulatory effect, a regulatory effect on prostaglandin production, etc. Therefore, a pharmaceutical composition comprising the benzazepine compound of the present invention as an active ingredient is useful as, for example a vasodilator, an antihypertensive agent, a water-diuretic agent, a platelet aggregation inhibitor, a ureotelic agent, an anti-heart failure agent, an anti-renal failure agent, etc.; and is effective in preventing or treating hypertension, edema, ascites, heart failure, renal dysfunction, syndrome of inappropriate secretion of vasopressin (syndrome of inappropriate secretion of antidiuretic hormone: SIADH), liver cirrhosis, hyponatremia, hypokalemia, diabetes, circulatory failure, motion sickness, water-metabolism disorder, renal failure, cerebral infarction, cardiac infarction, polycystic kidney diseases (PKD), various ischemic diseases, and the like.

The benzazepine compound of the present invention has features such as causing few side effects and achieving sustained drug efficacy.

DESCRIPTION OF EMBODIMENTS

The present invention is explained in detail below with reference to Reference Examples and Examples.

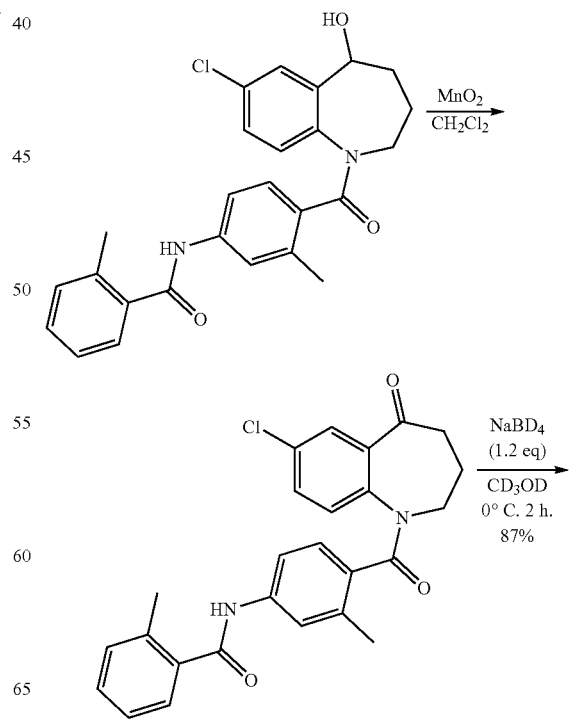

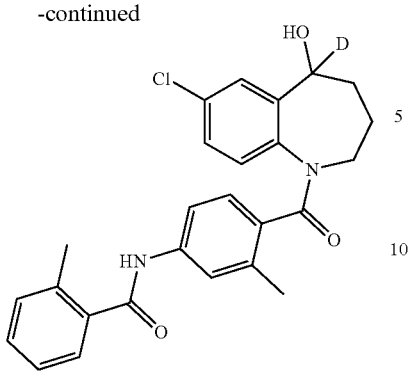

Reference Example 1

Production of N-(4-(7-chloro-5-oxo-2,3,4-trihydro-1H-benzo[b]azepine-1-carbonyl)-3-methylphenyl)-2-methylbenzamide Manganese dioxide (2 g) was added to a suspension of N-(4-(7-chloro-5-hydroxy-2,3,4,5-tetrahydro-1H-benzo[b]azepine-1-carbonyl)-3-methylphenyl)-2-methylbenzamide (2 g) in dichloromethane (40 mL), and the mixture was refluxed for 7 hours. After being cooled, the reaction mixture was filtered through Celite, washed with dichloromethane, and then purified by silica gel column chromatography (n-hexane:ethyl acetate=10:1→3:1) to obtain 0.94 g of N-(4-(7-chloro-5-oxo-2,3,4-trihydro-1H-benzo[b]azepine-1-carbonyl)-3-methylphenyl)-2-methylbenzamide.

Properties: Colorless amorphous powder $^1$H-NMR (CDCl$_3$) δppm 1.91-1.31 (2H, m), 2.43 (3H, s), 2.49 (3H, s), 2.89 (2H, t, J=6.3 Hz), 3.30-4.60 (2H, m), 6.48-7.00 (2H, m), 7.01-7.70 (8H, m), 7.78 (1H, s).

Example 1

Production of N-(4-(7-chloro-5-hydroxy-2,3,4-trihydro-5-deutero-1H-benzo[b]azepine-1-carbonyl)-3-methylphenyl)-2-methylbenzamide Sodium borodeuteride (0.045 g) was added to a solution of N-(4-(7-chloro-5-oxo-2,3,4-trihydro-1H-benzo[b]azepine-1-carbonyl)-3-methylphenyl)-2-methylbenzamide (0.4 g) in deuterated methanol (10 mL) at 0° C., and the mixture was stirred at the same temperature for 2 hours. Deuterium oxide (2 mL) was added to the resulting reaction mixture, and the mixture was stirred for 10 minutes. Water was added thereto, followed by extraction with ethyl acetate. The resulting water layer was subjected to extraction with ethyl acetate again. The ethyl acetate layers thus obtained were combined and dried over anhydrous magnesium sulfate. Subsequently, the solvent was distilled off and the residue was recrystallized from acetone-diethyl ether to obtain 0.35 g of N-(4-(7-chloro-5-hydroxy-2,3,4-trihydro-5-deutero-1H-benzo[b]azepine-1-carbonyl)-3-methylphenyl)-2-methylbenzamide.

Yield: 87%

Properties: White powder $^1$H-NMR (DMSO-d6, 80° C.) δppm 1.40-2.19 (4H, m), 2.36 (3H, s), 2.38 (3H, s), 3.35-4.94 (2H, br), 5.35 (1H, s), 6.56-7.70 (10H, m), 9.93 (1H, brs)

MS: (M$^+$, 449)

Melting point: 227.8° C.

Example 2

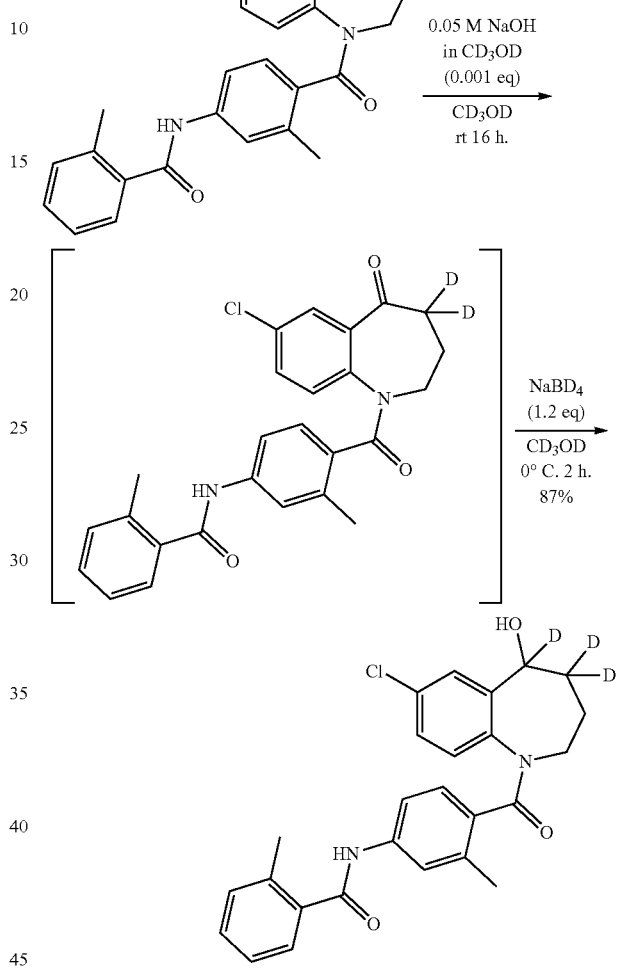

Production of N-(4-(7-chloro-2,3-dihydro-5-hydroxy-4,4,5-trideutero-1H-benzo[b]azepine-1-carbonyl)-3-methylphenyl)-2-methylbenzamide A 0.05 M sodium hydroxide deuterated methanol solution (13 μl) was added to a solution of N-(4-(7-chloro-5-oxo-2,3,4,5-tetrahydro-1H-benzo[b]azepine-1-carbonyl)-3-methylphenyl)-2-methylbenzamide (300 mg) in deuterated methanol (10 mL). The mixture was stirred under an argon atmosphere at room temperature. After stirring for 16 hours, elimination of the proton at the 4-position was confirmed by $^1$H-NMR. Sodium borodeuteride (0.037 g) was added to the reaction mixture at 0° C. and the mixture was stirred at the same temperature for 2 hours. Deuterium oxide (2 mL) was added to the resulting reaction mixture and stirred for 10 minutes. Water was added thereto, followed by extraction with ethyl acetate. The resulting water layer was subjected to extraction with ethyl acetate again. The ethyl acetate layers thus obtained were combined and dried over anhydrous magnesium sulfate. Subsequently, the solvent was distilled off, and the residue was recrystallized from acetone-diethyl ether to obtain 0.22 g of N-(4-(7-chloro-2,3-dihydro-5-hydroxy-4,4,5-trideutero-1H-benzo[b]azepine-1-carbonyl)-3-methylphenyl)-2-methylbenzamide.

Yield: 73%
Properties: White powder
$^1$H-NMR (DMSO-d6, 80° C.) δppm
1.51-2.06 (2H, m), 2.36 (3H, s), 2.38 (3H, s), 3.36-5.02 (2H, br), 5.34 (1H, s), 6.58-7.70 (10H, m), 9.94 (1H, brs)
MS: (M$^+$, 451)
Melting point: 225.1° C.

Reference Example 2

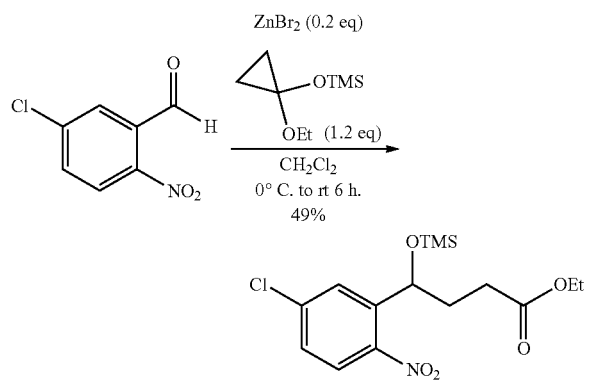

Production of ethyl 4-(5-chloro-2-nitrophenyl)-4-(trimethylsilyloxy)butanoate

After drying zinc bromide (1.21 g) by heating under reduced pressure for 15 minutes, 5-chloro-2-nitrobenzaldehyde (5.0 g) and dichloromethane (70 mL) were added thereto. [(1-Ethoxycyclopropyl)oxy]trimethylsilane (6.50 mL) was added to the resulting mixture dropwise at 0° C. and stirred at room temperature for 6 hours. After concentrating the reaction mixture under reduced pressure, the residue was purified by basic silica gel column chromatography (n-hexane:ethyl acetate=20:1→10:1) to obtain 4.76 g of ethyl 4-(5-chloro-2-nitrophenyl)-4-(trimethylsilyloxy)butanoate.

Yield: 49%
Properties: Yellow oily substance
$^1$H-NMR (CDCl$_3$) δppm
0.05 (9H, s), 1.26 (3H, t, J=7.1 Hz), 1.80-2.00 (1H, m), 2.01-2.20 (1H, m), 2.45 (2H, t, J=7.5 Hz), 4.13 (2H, q, J=7.1 Hz), 5.29-5.45 (1H, m), 7.37 (1H, dd, J=2.4 Hz, 8.7 Hz), 7.80 (1H, d, J=2.4 Hz), 7.91 (1H, d, J=8.7 Hz).

Reference Example 3

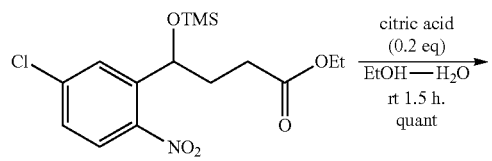

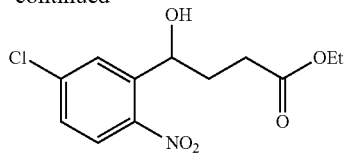

Production of ethyl 4-(5-chloro-2-nitrophenyl)-4-hydroxybutanoate

Citric acid (0.51 g) was added to a solution of ethyl 4-(5-chloro-2-nitrophenyl)-4-(trimethylsilyloxy)butanoate (4.76 g) in ethanol (25 mL) and water (5 mL) and stirred at room temperature for 1.5 hours. Water was added to the reaction mixture, followed by extraction with ethyl acetate. The ethyl acetate layer was washed with a saturated sodium chloride aqueous solution and dried over anhydrous magnesium sulfate. Subsequently, the solvent was distilled off and the residue was purified by silica gel column chromatography (n-hexane:ethyl acetate=20:1→10:1) to obtain 3.8 g of ethyl 4-(5-chloro-2-nitrophenyl)-4-hydroxybutanoate.

Properties: Pale yellow oily substance
$^1$H-NMR (CDCl$_3$) δppm
1.29 (3H, t, J=7.1 Hz), 1.91-2.09 (1H, m), 2.10-2.25 (1H, m), 2.51-2.72 (2H, m), 3.50 (1H, d, J=3.9 Hz), 4.18 (2H, q, J=7.1 Hz), 5.31-5.43 (1H, m), 7.39 (1H, dd, J=2.3 Hz, 8.7 Hz), 7.90 (1H, d, J=2.3 Hz), 7.95 (1H, d, J=8.7 Hz).

Reference Example 4

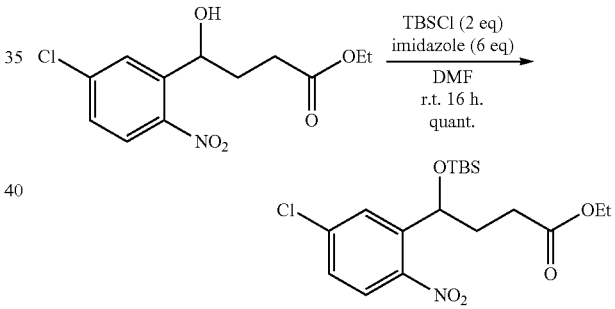

Production of ethyl 4-(tert-butyldimethylsilyloxy)-4-(5-chloro-2-nitrophenyl)butanoate Imidazole (5.4 g) and tert-butyldimethylsilyl chloride (3.98 g) were added to a solution of ethyl 4-(5-chloro-2-nitrophenyl)-4-hydroxybutanoate (3.8 g) in anhydrous dimethylformamide (25 mL), and stirred at room temperature for 16 hours. Water was added to the reaction mixture, followed by extraction with ethyl acetate. The ethyl acetate layer was washed with water three times and dried over anhydrous magnesium sulfate. Subsequently, the solvent was distilled off and the residue was purified by basic silica gel column chromatography (n-hexane:ethyl acetate=20:1→10:1) to obtain 5.3 g of ethyl 4-(tert-butyldimethylsilyloxy)-4-(5-chloro-2-nitrophenyl)butanoate with a quantitive yield.

Properties: Yellow oily substance
$^1$H-NMR (DMSO-d6) δppm
−0.19 (3H, s), 0.03 (3H, s), 0.84 (9H, s), 1.17 (3H, t, J=7.1 Hz), 1.81-2.11 (3H, m), 2.33-2.45 (1H, m), 4.02 (2H, q, J=7.1 Hz), 5.17-5.29 (1H, m), 7.64 (1H, dd, J=2.4 Hz, 8.7 Hz), 7.74 (1H, d, J=2.4 Hz), 8.01 (1H, d, J=8.7 Hz).

Reference Example 5

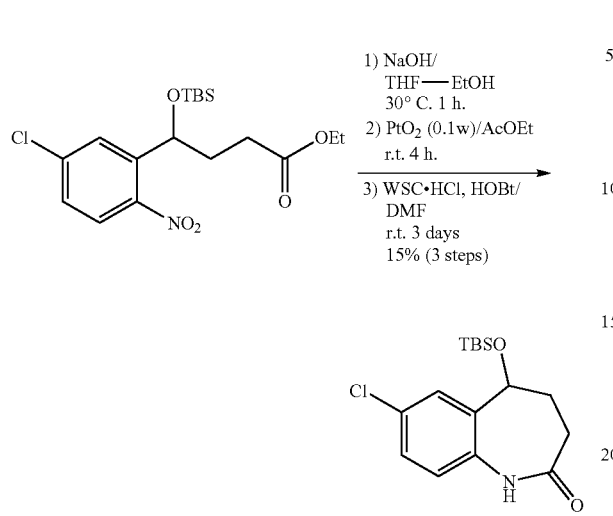

Production of 5-(tert-butyldimethylsilyloxy)-7-chloro-3,4,5-trihydro-1H-benzo[b]azepin-2(3H)-one A 5M-sodium hydroxide aqueous solution (3.43 mL, 17.2 mmol) was added to a solution of ethyl 4-(tert-butyldimethylsilyloxy)-4-(5-chloro-2-nitrophenyl)butanoate (4.6 g) in tetrahydrofuran:ethanol (1:1)(40 mL) and stirred at 30° C. for 1 hour. A 10% citric acid aqueous solution was added to the reaction mixture, followed by extraction with ethyl acetate. The ethyl acetate layer was washed with a saturated sodium chloride aqueous solution and dried over anhydrous magnesium sulfate. Subsequently, the solvent was distilled off and ethyl acetate (40 mL) was added to the residue. After adding platinum oxide (0.26 g) under a nitrogen atmosphere, the mixture was stirred at 1 atm under a hydrogen atmosphere for 3 hours. The platinum oxide was filtered through Celite and washed with ethyl acetate. The filtrate was concentrated, and 1-ethyl-3-(3-dimethylaminopropyl)carbodiimide.hydrochloride (2.63 g), 1-hydroxybenzotriazole hydrate (2.1 g), and triethylamine (1.91 mL) were added to a solution of anhydrous DMF (60 mL). The reaction mixture was stirred at room temperature for 3 days, and water was added thereto, followed by extraction with ethyl acetate. The resulting water layer was subjected to extraction with ethyl acetate again. The ethyl acetate layers obtained were combined, washed with water three times, and dried over anhydrous magnesium sulfate. Subsequently, the solvent was distilled off and the residue was purified by basic silica gel column chromatography (n-hexane:ethyl acetate=20:1→48:1) to obtain 0.55 g of 5-(tert-butyldimethylsilyloxy)-7-chloro-3,4,5-trihydro-1H-benzo[b]azepin-2(3H)-one.

Yield: 15%
Properties: Colorless amorphous powder
$^1$H-NMR (CDCl$_3$) δppm
0.01 (3H, s), 0.08 (3H, s), 0.93 (9H, s), 1.89-2.06 (2H, m), 2.20-2.36 (2H, m), 2.43-2.67 (1H, m), 4.96 (1H, dd, J=7.1 Hz, 10.1 Hz), 6.87 (1H, d, J=8.4 Hz), 7.16 (1H, brs), 7.23 (1H, dd, J=2.1 Hz, 8.4 Hz), 7.58 (1H, d, J=2.1 Hz).

Reference Example 6

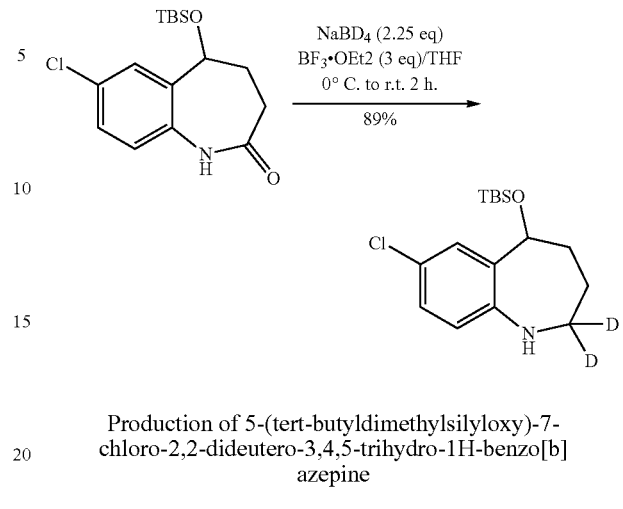

Production of 5-(tert-butyldimethylsilyloxy)-7-chloro-2,2-dideutero-3,4,5-trihydro-1H-benzo[b]azepine Sodium borodeuteride (424 mg) was added to a solution of 5-(tert-butyldimethylsilyloxy)-7-chloro-3,4,5-trihydro-1H-benzo[b]azepin-2(3H)-one (550 mg) in anhydrous THF (30 mL) at 0° C., and a boron trifluoride diethyl ether complex (0.855 mL) was added thereto dropwise at the same temperature. After stirring the resulting mixture at 0° C. for 1 hour, sodium borodeuteride (210 mg) was added thereto. After stirring the mixture at room temperature for 2 hours, deuterium oxide (4 mL) was added thereto dropwise at 0° C., followed by stirring at the same temperature for 15 minutes. Subsequently, methanol (10 mL) was added to the reaction mixture and stirred at room temperature for 20 minutes. Water was added to the reaction mixture, followed by extraction with ethyl acetate. The resulting water layer was subjected to extraction with ethyl acetate again. The ethyl acetate layers obtained were combined and dried over anhydrous magnesium sulfate. Subsequently, the solvent was distilled off and the residue was purified by basic silica gel column chromatography (n-hexane:ethyl acetate=20:1→10:1) to obtain 470 mg of 5-(tert-butyldimethylsilyloxy)-7-chloro-2,2-dideutero-3,4,5-trihydro-1H-benzo[b]azepine.

Properties: Colorless amorphous powder
$^1$H-NMR (CDCl$_3$) δppm
0.07 (3H, s), 0.09 (3H, s), 0.95 (9H, s), 1.70-1.90 (2H, m), 1.94-2.12 (1H, m), 3.58-3.80 (1H, m), 4.61-4.79 (1H, m), 6.63 (1H, d, J=8.3 Hz), 7.00 (1H, dd, J=2.5 Hz, 8.3 Hz), 7.48 (1H, dd, J=0.9 Hz, 2.5 Hz).

Example 3

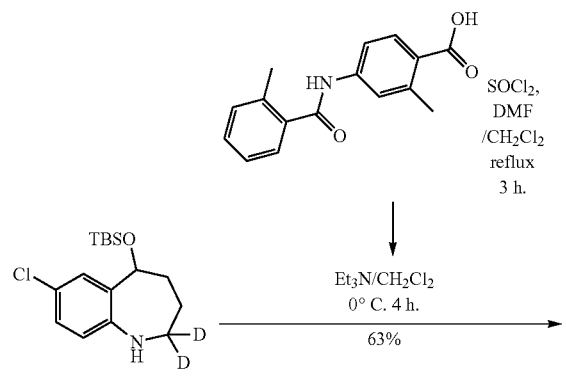

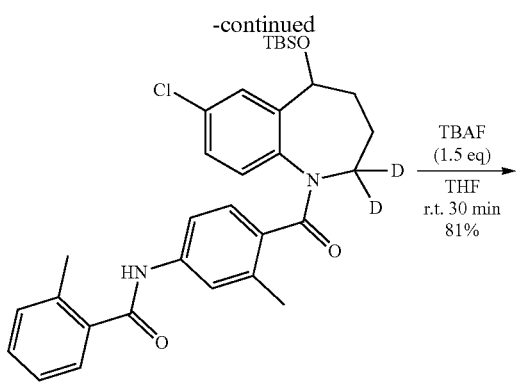

Production of N-(4-(7-chloro-5-hydroxy-2,2-dideutero-3,4,5-trihydro-1H-benzo[b]azepine-1-carbonyl)-3-methylphenyl)-2-methylbenzamide Thionyl chloride (0.14 mL) and dimethylformamide (1.2 μl) were added to a suspension of 2-methyl-4-(2-methylbenzamide)benzoic acid (450 mg) in dichloromethane (30 mL), and the mixture was refluxed for 3 hours. The reaction mixture was concentrated under reduced pressure and azeotroped with toluene twice.

Triethylamine (0.24 mL) and a solution of the acid chloride prepared above in dichloromethane (5 mL) were sequentially added dropwise to a solution of 5-(tert-butyldimethylsilyloxy)-7-chloro-2,2-dideutero-3,4,5-trihydro-1H-benzo[b]azepine (500 mg) in dichloromethane (50 mL) at 0° C. After stirring at the same temperature for 4 hours, water was added to the reaction mixture, followed by extraction with dichloromethane. The dichloromethane layer was washed with a saturated sodium chloride aqueous solution, and dried over anhydrous magnesium sulfate. Subsequently, the solvent was distilled off and the residue was purified by basic silica gel column chromatography (n-hexane:ethyl acetate=10:1→3:1) to obtain 570 mg of N-(4-(5-(tert-butyldimethylsilyloxy)-7-chloro-2,2-dideutero-3,4,5-trihydro-1H-benzo[b]azepine-1-carbonyl)-3-methylphenyl)-2-methylbenzamide. A THF solution (1.51 mL) of 1N-tetrabutylammonium fluoride was added to a solution of N-(4-(5-(tert-butyldimethylsilyloxy)-7-chloro-2,2-dideutero-3,4,5-trihydro-1H-benzo[b]azepine-1-carbonyl)-3-methylphenyl)-2-methylbenzamide obtained above in THF (40 mL) at 0° C. The resulting mixture was stirred at room temperature for 30 minutes and 1M-HCl was added thereto at 0° C., followed by extraction with ethyl acetate. The ethyl acetate layer was washed with water and dried over anhydrous magnesium sulfate. Subsequently, the solvent was distilled off and the residue was recrystallized from acetone-diethyl ether to obtain 370 mg of N-(4-(7-chloro-5-hydroxy-2,2-dideutero-3,4,5-trihydro-1H-benzo[b]azepine-1-carbonyl)-3-methylphenyl)-2-methylbenzamide.

Properties: White powder
¹H-NMR (DMSO-d6, 80° C.) δppm
1.41-2.06 (2H, m), 2.36 (3H, s), 2.38 (3H, s), 4.78-4.96 (1H, m), 5.37 (1H, d, J=4.3 Hz), 6.61-7.69 (10H, m), 9.94 (1H, brs)
MS: (M⁺, 450)
Melting point: 223.7° C.

Example 4

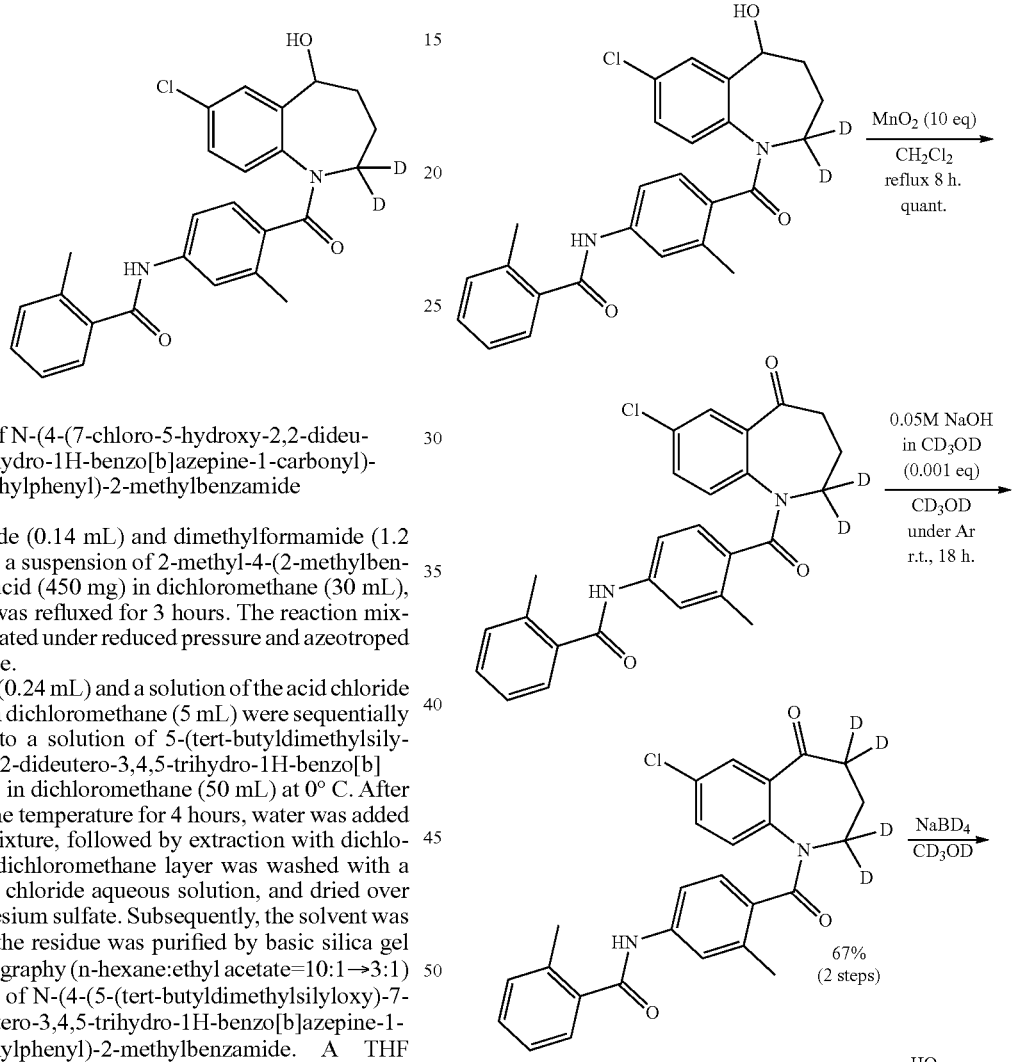

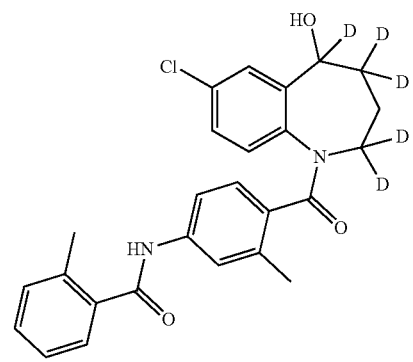

Production of N-(4-(7-chloro-5-oxo-2,2-dideutero-3, 4-dihydro-1H-benzo[b]azepine-1-carbonyl)-3-methylphenyl)-2-methylbenzamide Manganese dioxide (482 mg) was added to a suspension of N-(4-(7-chloro-5-hydroxy-2,2-dideutero-3,4,5-trihydro-1H-benzo[b]azepine-1-carbonyl)-3-methylphenyl)-2-methylbenzamide (0.25 g) in dichloromethane (50 mL), and the mixture was refluxed for 8 hours. The reaction mixture was cooled and then filtered through Celite. The filtered object was washed with dichloromethane, and the residue obtained by concentrating the filtrate was purified by silica gel column chromatography (n-hexane:ethyl acetate=10:1→3:1) to obtain 0.24 g of N-(4-(7-chloro-5-oxo-2,2-dideutero-3,4-dihydro-1H-benzo[b]azepine-1-carbonyl)-3-methylphenyl)-2-methylbenzamide.

Properties: Colorless amorphous powder $^1$H-NMR (CD$_3$OD, 50° C.) δppm 1.98-2.18 (2H, m), 2.38 (3H, s), 2.41 (3H, s), 2.73-2.91 (2H, m), 6.73-7.78 (10H, m).

Production of N-(4-(7-chloro-5-hydroxy-2,2,4,4,5-pentadeutero-1H-benzo[b]azepine-1-carbonyl)-3-methylphenyl)-2-methylbenzamide A 0.05 M sodium hydroxide deuterated methanol solution (11 μL) was added to a solution of N-(4-(7-chloro-5-oxo-2,2-dideutero-3,4-dihydro-1H-benzo[b]azepine-1-carbonyl)-3-methylphenyl)-2-methylbenzamide (250 mg) in deuterated methanol (10 mL), and the mixture was stirred under an argon atmosphere at room temperature. After stirring for 18 hours, elimination of the proton at the 4-position was confirmed by $^1$H-NMR. The reaction mixture was concentrated and suspended in deuterated methanol (10 mL). Sodium borodeuteride (0.030 g) was added to the suspension at 0° C. and the mixture was stirred at the same temperature for 2 hours. Deuterium oxide (2 mL) was added to the resulting reaction mixture and stirred for 20 minutes. Water was added thereto, followed by extraction with ethyl acetate. The resulting water layer was subjected to extraction with ethyl acetate again. The ethyl acetate layers obtained were combined and dried over anhydrous magnesium sulfate. Subsequently, the solvent was distilled off and the residue was recrystallized from acetone-diethyl ether to obtain 0.17 g of N-(4-(7-chloro-5-hydroxy-2,2,4,4,5-pentadeutero-1H-benzo[b]azepine-1-carbonyl)-3-methylphenyl)-2-methylbenzamide.

Properties: White powder $^1$H-NMR (DMSO-d6, 80° C.) δppm 1.60-2.00 (2H, m), 2.36 (3H, m), 2.38 (3H, s), 5.34 (1H, s), 6.51-7.70 (10H, m), 9.93 (1H, brs)

MS: (M$^+$, 453)

Melting point: 224.7° C.

The compound produced when the elimination of the proton at the 4-position was confirmed by $^1$H-NMR was N-(4-(7-chloro-5-oxo-2,2,4,4-tetradeutero-3-hydro-1H-benzo[b]azepine-1-carbonyl)-3-methylphenyl)-2-methylbenzamide, whose NMR spectra are shown below.

$^1$H-NMR (CD$_3$OD, 50° C.) δppm 1.94-2.19 (2H, m), 2.38 (3H, s), 2.41 (3H, s), 6.76-7.78 (10H, m).

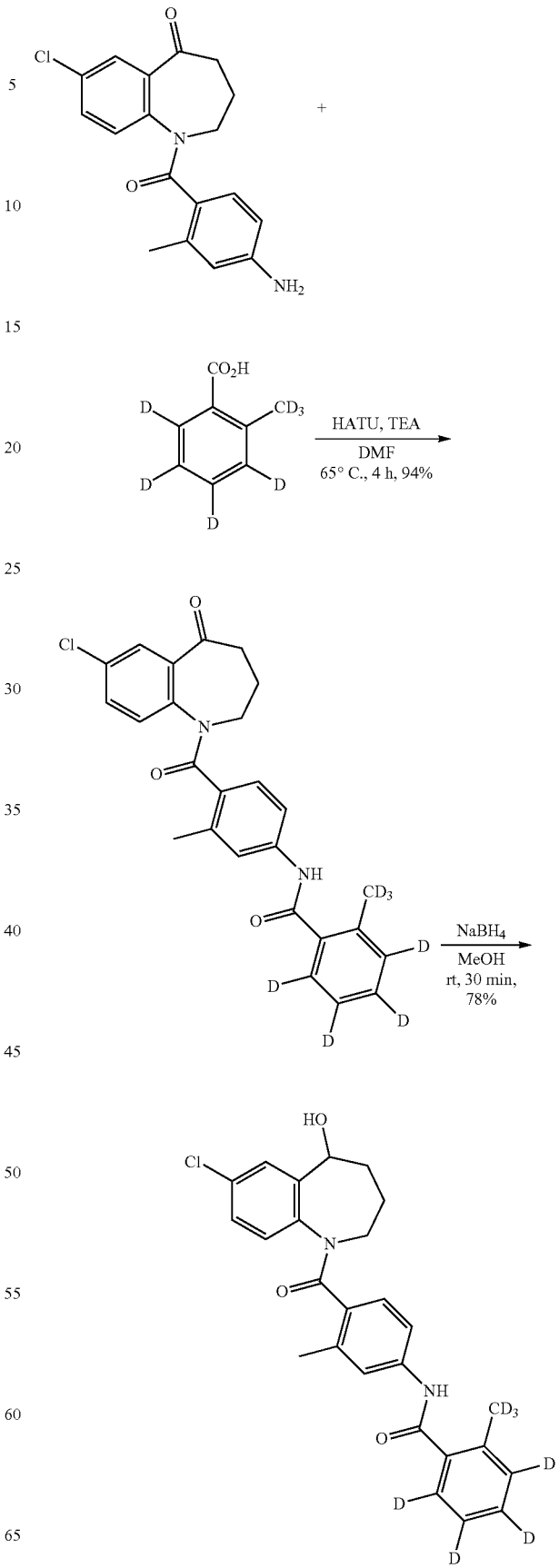

Reference Example 7

Production of N-{4-(7-chloro-5-oxo-2,3,4-trihydro-1H-benzo[b]azepine-1-carbonyl)-3-methylphenyl}-3,4,5,6-tetradeutero-2-trideutero methylbenzamide Hexafluorophosphoric 2-(7-aza-1H-benzotriazol-1-yl)-1,1,3,3-tetramethyluronium (3.04 g) was added to a solution of 1-(4-amino-2-methylbenzoyl)-7-chloro-2,3,4-trihydro-1H-benzo[b]azepin-5(2H)-one (2.39 g), 3,4,5,6-tetradeutero-2-trideutero methylbenzoic acid (1.04 g) and triethylamine (1.4 mL, 10 mmol) in dimethylformamide (24 mL). The mixture was then stirred at 65° C. under a nitrogen atmosphere for 4 hours. After concentrating the reaction mixture, 0.1 N hydrochloric acid (100 mL) was added thereto, followed by extraction with ethyl acetate (100 mL). The organic layer was sequentially washed with saturated sodium bicarbonate water and a saturated sodium chloride aqueous solution, and dried over anhydrous sodium sulfate. Subsequently, the solvent was distilled off and the resulting residue was purified by medium pressure silica gel column chromatography (dichloromethane→dichloromethane/ethyl acetate=3/1) to obtain 3.1 g of N-{4-(7-chloro-5-oxo-2,3,4-trihydro-1H-benzo[b]azepine-1-carbonyl)-3-methylphenyl}-3,4,5,6-tetradeutero-2-trideutero methylbenzamide in the form of a yellowish-brown amorphous solid.

Properties: yellowish-brown amorphous powder
$^1$H-NMR (300 MHz, CDCl$_3$) δppm
1.86-2.31 (2H, m), 2.40 (3H, s), 2.87 (2H, t, J=6.3 Hz), 3.16-5.04 (2H, br), 6.42-7.41 (4H, m), 7.45-7.70 (2H, m), 7.76 (1H, br.s).

Example 5

Production of N-{4-(7-chloro-5-hydroxy-2,3,4,5-tetrahydro-1H-benzo[b]azepine-1-carbonyl)-3-methylphenyl}-3,4,5,6-tetradeutero-2-trideutero methylbenzamide Sodium borohydride (300 mg) was added to a suspension of N-{4-(7-chloro-5-oxo-2,3,4,5-tetrahydro-1H-benzo[b]azepine-1-carbonyl)-3-methylphenyl}-3,4,5,6-tetradeutero-2-trideutero methylbenzamide (3.0 g) in methanol (30 mL) at 0° C. The mixture was then stirred at room temperature for 30 minutes. 1 N hydrochloric acid (40 mL) and water (100 mL) were added to the reaction mixture, followed by extraction with ethyl acetate (150 mL). The organic layer was sequentially washed with saturated sodium bicarbonate water and a saturated sodium chloride aqueous solution, and dried over anhydrous sodium sulfate. Subsequently, the solvent was distilled off and the resulting residue was purified by medium pressure silica gel column chromatography (dichloromethane/ethyl acetate=3/1→1/1). The residue was recrystallized from hydrous methanol to obtain N-{4-(7-chloro-5-hydroxy-2,3,4,5-tetrahydro-1H-benzo[b]azepine-1-carbonyl)-3-methylphenyl}-3,4,5,6-tetradeutero-2-trideutero methylbenzamide (2.36 g) in the form of a white powder.

Properties: White powder
Melting point: 225-228° C. (methanol-water).

Pharmacological Test 1

Test Method and Data Analytical Method

HeLa cells expressing human V1a-receptors (V1a-HeLa) cultured in a 12-well plate or HeLa cells expressing human V2-receptors (V2-HeLa) cultured in a 24-well plate were washed with D-PBS twice.

In a [$^3$H]AVP saturation binding assay, [$^3$H]AVP with various concentrations (V1a-HeLa; 0.4 nM to 7 nM, V2-HeLa; 0.3 nM to 6 nM) were added to each well containing the reaction mixture (DMEM-0.3% BSA) and allowed to react in the presence and absence of AVP (1 μM). In a [$^3$H]AVP binding-inhibition assay, in the presence of each compound with various concentrations (V1a-HeLa; 1 nM to 100 nM, V2-HeLa; 0.1 nM to 10 nM), [$^3$H]AVP (V1a-HeLa; 3.3 nM to 3.7 nM, V2-HeLa; 1.4 nM to 1.7 nM) were added to each well containing the reaction mixture and allowed to react.

The contents of the plates described above were allowed to react at 4° C. for 2 hours, and washed with D-PBS twice. Cells were collected using 0.1 N NaOH containing SDS (0.1%), and the radioactivity of [$^3$H]AVP was measured by liquid scintillation counter. The measurement described above was performed in duplicate.

The dissociation constant ($K_d$) and the number of receptors ($B_{max}$) were obtained by analyzing the results of the [$^3$H]AVP saturation binding assay with the Scatchard plot. In the [$^3$H]AVP binding-inhibition assay, the binding ratio of [$^3$H]AVP in the presence of the compound was calculated by the following equation.

$$\text{Binding ratio (\%)} = (B-NSB)/(TB-NSB) \times 100$$

(B is the total binding of [$^3$H]AVP in the presence of each compound; NSB is the total binding of [$^3$H]AVP in the presence of unlabeled AVP (1 μM); and TB is the total binding of [$^3$H]AVP in the absence of unlabeled AVP 1 μM.)

Using the binding ratio obtained above, the concentration of each compound at which binding of [$^3$H]AVP was inhibited by 50% (IC$_{50}$) was calculated. Using the IC$_{50}$ obtained, the inhibition constant ($K_i$) of each compound was calculated from the following equation.

$$K_i = IC_{50}/(1+[L]/K_d)$$

($k_d$ is the dissociation constant of [$^3$H]AVP, and [L] is the concentration of [$^3$H]AVP used in the experiment.)

As a result, the presence of excellent vasopressin antagonistic activity was confirmed.

Pharmacological Test 2

Metabolic Stability Assay

The Reaction System and Incubation

The following reaction system was prepared with reference to the method disclosed by Obach, and that disclosed by Jones et al. (References 1 and 2), and the metabolic stability thereof was evaluated. Note that the human liver microsomes used were purchased from BD Gentest. The test compound was dissolved in DMSO to have a concentration of 10 mM and diluted with acetonitrile in such a manner that its concentration became 100 μM.

Reaction System

| | |
|---|---|
| Test compound | 1 μM |
| Liver microsome | 0.2 mg/mL |
| Coenzyme (NADPH/NADH) | 1 mM |
| Magnesium chloride | 5 mM |
| 100 mM Phosphate buffer (pH 7.4) | |
| Number of experiments: | n = 4 |

Reaction Conditions

A reaction system without a coenzyme was preincubated at 37° C. for 5 minutes, and a coenzyme was then added to start the reaction. After the addition of the coenzyme, the incubation was performed at selected time intervals, i.e., 0, 5, 10, 20, 30 and 60 minutes to extract a portion of the reaction mixture.

The extracted reaction mixture was added to an acetonitrile solution containing an internal standard substance and the reaction was then terminated.

Analytical Method

After the reaction was terminated, the resulting mixture was centrifuged, the supernatant was poured into a liquid chromatograph tandem mass spectrometer (LC-MS/MS) to determine the level of unchanged substance remaining in the reaction system. Ionization was performed by electro-spray ionization (ESI) in a positive ion detection mode. Here, selected reaction monitoring (MRM) using preset precursor ions and product ions was employed.

Data Analysis

The remaining ratio of the test compound was calculated by the following equation.

Remaining ratio=(peak area of the test compound at the reaction time of $t$ minutes/peak area of the internal standard substance)÷(peak area of the test compound at the reaction time of 0 minutes/peak area of the internal standard substance)

A nonlinear least-squares analysis was performed in terms of the remaining ratio and incubation time to obtain the elimination rate constant ($0.693/t_{1/2}$), and, further, the hepatic intrinsic clearance (Clint) was obtained using the following Formula (1).

$$\text{Clint } (\mu L/\min/mg)=(0.693/t_{1/2})\div 0.2 \text{ (mg/mL)} \times 1000 \quad (1)$$

Regarding the hepatic intrinsic clearance of each test compound obtained above, a group comparison was performed using two-tailed Dunnett's test to determine the significant difference from that of tolvaptan.

Results

The metabolic stability in human liver microsomes of tolvaptan and its deuterium substituted analogues (Example 4) was evaluated. The hepatic intrinsic clearance (Clint), which is an index for metabolic stability, of each test is shown below.

Tolvaptan: 214±4.3 (µL/min/mg)

Example 4: 166±5.3* (µL/min/mg)

(two-tailed Dunnett's test,*: p<0.001)

The compound of Example 4 exhibited significantly improved metabolic stability compared to tolvaptan.

REFERENCE DOCUMENTS

1. R. S. Obach. Drug Metab. Dispos. 1999(27): 1,350-1,359
2. H. Jones and J. B. Houston, Drug Metab Dispos, 2004 (32): 973-982

The invention claimed is:

1. A benzazepine compound selected from the group consisting of:
   (1) N-(4-(7-chloro-5-hydroxy-2,3,4-trihydro-5-deutero-1H-benzo[b]azepine-1-carbonyl)-3-methylphenyl)-2-methylbenzamide,
   (2) N-(4-(7-chloro-2,3-dihydro-5-hydroxy-4,4,5-trideutero-1H-benzo[b]azepine-1-carbonyl)-3-methylphenyl)-2-methylbenzamide,
   (3) N-(4-(7-chloro-5-hydroxy-2,2-dideutero-3,4,5-trihydro-1H-benzo[b]azepine-1-carbonyl)-3-methylphenyl)-2-methylbenzamide, and
   (4) N-(4-(7-chloro-5-hydroxy-2,2,4,4,5-pentadeutero-1H-benzo[b]azepine-1-carbonyl)-3-methylphenyl)-2-methylbenzamide,
   or a salt thereof.

2. A pharmaceutical composition or a salt thereof comprising, as an active ingredient, the benzazepine compound of claim 1, and a pharmaceutically acceptable carrier.

3. A vasopressin antagonist comprising, as an active ingredient, the benzazepine compound or a salt thereof of claim 1.

4. The pharmaceutical composition according to claim 2, which is for preventing or treating at least one disease selected from the group consisting of hypertension, edema, ascites, heart failure, renal dysfunction, syndrome of inappropriate secretion of antidiuretic hormone (SIADH), liver cirrhosis, hyponatremia, hypokalemia, diabetes, circulatory failure, motion sickness, water-metabolism disorder, renal failure, cerebral infarction, cardiac infarction, and polycystic kidney disease (PKD).

5. The pharmaceutical composition according to claim 2, which is for use as at least one drug selected from the group consisting of vasodilators, antihypertensive agents, water-diuretic agents, platelet aggregation inhibitors, ureotelic agents, anti-heart failure agents, and anti-renal failure agents.

6. A method for treating at least one disease selected from the group consisting of hypertension, edema, ascites, heart failure, renal dysfunction, syndrome of inappropriate secretion of vasopressin (syndrome of inappropriate secretion of antidiuretic hormone: SIADH), liver cirrhosis, hyponatremia, hypokalemia, diabetes, circulatory failure, motion sickness, water-metabolism disorder, renal failure, cerebral infarction, cardiac infarction, and polycystic kidney diseases (PKD), the method comprising administering the benzazepine compound or a salt thereof of claim 1 to a human or animal.

7. A benzazepine compound, which is (3) N-(4-(7-chloro-5-hydroxy-2,2-dideutero-3,4,5-trihydro-1H-benzo[b]azepine-1-carbonyl)-3-methylphenyl)-2-methylbenzamide or a salt thereof.

8. A benzazepine compound, which is (4) N-(4-(7-chloro-5-hydroxy-2,2,4,4,5-pentadeutero-1H-benzo[b]azepone-1-carbonyl)-3-methylphenyl)-2-methylbenzamide or a salt thereof.

* * * * *